United States Patent
Yoshizaki et al.

(10) Patent No.: US 8,173,126 B2
(45) Date of Patent: May 8, 2012

(54) BLOOD VEGF LEVEL-LOWERING AGENT CONTAINING IL-6 ANTAGONIST AS THE ACTIVE INGREDIENT

(75) Inventors: Kazuyuki Yoshizaki, Ashiya (JP); Norihiro Nishimoto, Minoh (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/812,296

(22) Filed: Jun. 18, 2007

(65) Prior Publication Data

US 2007/0243189 A1   Oct. 18, 2007

Related U.S. Application Data

(63) Continuation of application No. 10/399,779, filed as application No. PCT/JP00/07603 on Oct. 27, 2000, now abandoned.

(51) Int. Cl.
*A61K 39/395* (2006.01)
*A61P 7/00* (2006.01)

(52) U.S. Cl. ............... 424/133.1; 424/143.1; 424/158.1; 514/8.1; 514/13.2

(58) Field of Classification Search ......................... None
See application file for complete search history.

(56) References Cited

U.S. PATENT DOCUMENTS

| | | | |
|---|---|---|---|
| 5,795,965 A | 8/1998 | Tsuchiya et al. | |
| 5,888,510 A | 3/1999 | Kishimoto et al. | |

FOREIGN PATENT DOCUMENTS

| | | |
|---|---|---|
| EP | 0 983 767 A1 | 3/2000 |
| JP | 5-148156 A | 6/1993 |

OTHER PUBLICATIONS

Soker et al., Journal of Biological Chemistry, 1993. vol. 286 pp. 7685-7691.*
Higuchi et al. Gene, 1994. vol. 141, pp. 155-162.*
Lu et al. Cancer Journal, 1997, vol. 10, No. 10, pp. 256-261.*
Paleolog e, European Journal of Clinical Investigation, 1998, vol. 28, (Suppl 1), (a36, 201).*
Nishi et al, British Journal of Haematology, 1999, 104, 482-485.*
Nakaharal et al., "Cytokine-Dependent Vascularization in Chronic Inflammation Pathology", vol. 20, No. 4, (Jul. 2000).
Nishi et al., "Increased Expression of Vascular Endothelial Growth Factor (VEGF) in Proliferation in the Affected Lymph Node," abstract, Leukemia and Lymphoma, Jul. 2000, vol. 38, Nos. 3-4, pp. 387-394.
Hojo et al., "Interaction Between Human Monocytes and Vascular Smooth Muscle Cells Induces Vascular Endotheli-al Growth Factor Expression," Atherosclerosis, May 2000, vol. 150, No. 1, pp. 53-70.
Cohen et al., "Interleukin 6 Induces the Expression of Vascular Endothelial Growth Factor," The Journal of Biological Chemistry, 1996, vol. 271, No. 2, pp. 736-741.
Nishimoto et al., "Improvement in Castleman's Disease by Humanized Anti-Interleukin-6 Receptor Antibody Therapy," Blood, Jan. 2000, vol. 95, No. 1, pp. 56-61.
Beck et al., "Alleviation of Systemic Manifestations of Castleman's Disease by Monoclonal Anti-Interleukin-5 Antibody," The New England Journal of Medicine, 1994, vol. 330, No. 9, pp. 602-605.
Foss et al., "Expression of Vascular Endothelialgrowth Factor in Lymphomas and Castleman's Disease," Journal of Pathology, 1997, vol. 183, No. 1, pp. 44-50.
Sato et al., "Reshaping of Human Antibody to Inhibit the Interleukin 6 Dependent Tumor Cell Growth," Cancer Research, vol. 53, Feb. 1993, 851-856.

* cited by examiner

*Primary Examiner* — Bridget E Bunner
*Assistant Examiner* — Fozia Hamud
(74) *Attorney, Agent, or Firm* — Foley & Lardner LLP

(57) ABSTRACT

A blood vascular endothelial growth factor (VEGF) level-lowering agent comprising an interleukin-6 (IL-6) antagonist as an active ingredient.

19 Claims, 1 Drawing Sheet

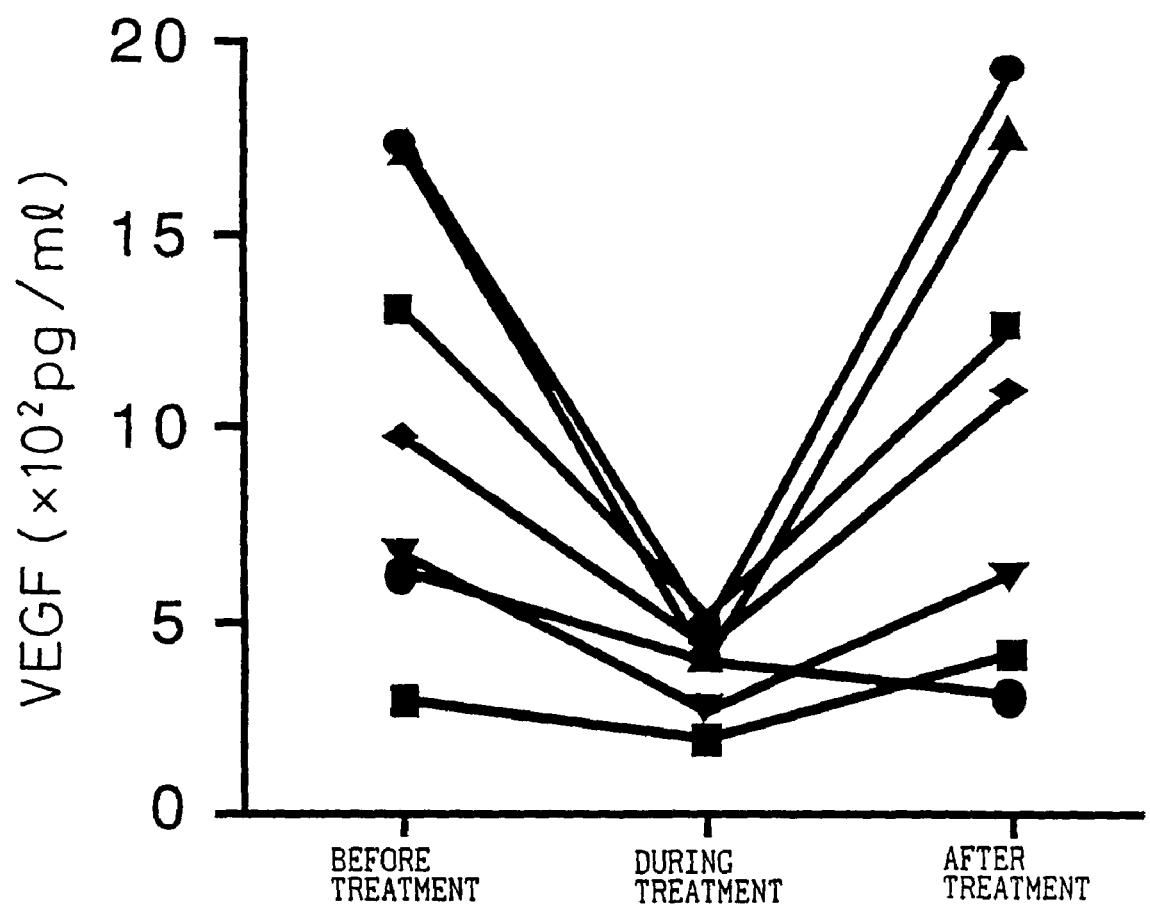

BLOOD VEGF LEVEL-LOWERING AGENT CONTAINING IL-6 ANTAGONIST AS THE ACTIVE INGREDIENT

CROSS REFERENCE TO RELATED APPLICATIONS

This application is a Continuation of application Ser. No. 10/399,779, filed Apr. 25, 2003, which is the U.S. National Stage application of PCT/JP00/07603, filed Oct. 27, 2000.

TECHNICAL FIELD

The present invention relates to a blood vascular endothelial growth factor (VEGF) level-lowering agent and a cartilage degradation inhibitor, etc. comprising an interleukin-6 (IL-6) antagonist as an active ingredient.

BACKGROUND ART

IL-6is a cytokine called B-cell stimulating factor 2 (BSF2) or interferon β2. IL-6 was discovered as a differentiation factor responsible for activation of B-lymphatic cells (Hirano, T. et al., Nature (1986) 324, 73-76). Thereafter, it was found to be a multifunctional cytokine that influences the function of various cells (Akira, S. et al., Adv. in Immunology (1993) 54, 1-78). IL-6 has been reported to induce the maturing of T lymphatic cells (Lotz, M. et al., J. Exp. Med. (1988) 167, 1253-1258).

IL-6 propagates its biological activity through two proteins on the cell. One of them is a ligand-binding protein with a molecular weight of about 80 kD to which IL-6 binds (Taga T. et al., J. Exp. Med. (1987) 166, 967-981; Yamasaki, K. et al., Science (1987) 241, 825-828). IL-6 receptor occurs not only in a membrane-bound form that penetrates and is expressed on the cell membrane but also as a soluble IL-6 receptor consisting mainly of the extracellular region.

The other protein is non-ligand-binding membrane-bound protein gp130 with a molecular weight of about 130 kD that takes part in signal transduction. IL-6 and IL-6 receptor form an IL-6/IL-6 receptor complex, to which gp130 is bound, and thereby the biological activity of IL-6 is propagated into the cell (Taga et al., Cell (1989) 58, 573-581).

IL-6 antagonists are substances that inhibit the transduction of IL-6 biological activities. Up to now, there have been known antibodies to IL-6 (anti-IL-6 antibodies), antibodies to IL-6 receptor (anti-IL-6 receptor antibodies), antibodies to gp130 (anti-gp130 antibodies), reshaped IL-6,IL-6 or IL-6 receptor partial peptides, and the like.

Antibodies to IL-6 receptor have been described in a number of reports (Novick D. et al., Hybridoma (1991) 10, 137-146; Huang, Y. W. et al., Hybridoma (1993) 12, 621-630; international Patent Application WO 95-09873; French Patent Application FR 2694767; and U.S. Pat. No. 5,216,128). A humanized PM-1 antibody was obtained by implanting the complementarity determining region (CDR) of one of them, a mouse antibody PM-1 (Hirata et al., J. Immunology (1989) 143, 2900-2906), into a human antibody (International Patent Application WO 92-19759).

Castleman's disease is a disease first described by Castleman in 1956 as the hypertrophy of lymph nodes in the mediastinum similar to thymoma, in which the lymph nodes display two characteristics: (1) the hypertrophy of lymph follicles, and (2) angiogenesis associated with hyalinization and proliferation of endothelial cells (hyaline vascular type). In addition, it was found that Castleman's disease has another type (plasma cell type) in which many plasma cells are seen in interfollicular stroma. Multicentric Castleman's disease (MCD) is also characterized by the systemic occurrence of lymph nodes having similar histological features. There is no established method of treatment for MCD. Complications or prognostic factors include secondary amyloidosis, interstitial pneumonia, malignant lymphoma, plasmacytoma, Kaposi's sarcoma etc., and thus treatments effective for Castleman's disease are considered also effective for the prevention and treatment of these complications.

On the other hand, angiogenesis is a phenomenon in which new blood vessels are formed during the processes of inflammation, wound healing and cancerous growth, and it is known that vascular endothelial precursor cells in the blood stream, in addition to those formed de novo from the existing blood vessels, contribute to angiogenesis. As diseases in which angiogenesis is involved, there can be mentioned cancer, interstitial pneumonia, rheumatism, Kaposi's sarcoma, psoriasis, diabetic retinitis and the like, and drugs that inhibit angiogenesis are believed to be effective as preventive and/or therapeutic agents for these diseases. The proliferation and migration of vascular endothelial cells are controlled by growth factors such as FGF, HGF, PDGF, TGF-β and VEGF, and cytokines such as IL-1, IL-6,IL-8, TNF, INF-α and IFN-β. It is very difficult to predict how individual cytokines affect angiogenesis since not only does one cytokine has multiple effects but, at the same time, a plurality of cytokines have similar effects.

On the effect of IL-6 on angiogenesis, there are reports that suggest that IL-6 promotes angiogenesis as in a report (Aoki Y. et al., Blood, 93(12):40344, (1999)) that suggests viral IL-6 (vIL-6) stimulates VEGF production in NIH3T3 cells in an in vitro study, and a report (Cohen T. et al., J. Biol. Chem., 271(2):736 (1996)) that suggests IL-6 induces the expression of VEGF, whereas there is a report (Japanese Unexamined Patent Publication (Kokai) No. 4-202139) that indicates that IL-6 inhibits angiogenesis by inhibiting the formation of blood walls by suppressing motility such as the migration of vascular endothelial cells. Furthermore, it has also been reported that the administration of a humanized anti-IL-6 receptor antibody tended to reduce angiogenesis in patients with Castleman's disease (Nishimoto et. al., Blood, 95(1):56-61 (2000)), and in a report (Foss H-D, et al., J. Pathology, 183:44 (1997)) that investigated the expression of VEGF in Castleman's disease and the association of IL-6 and VEGF has been considered a subject that needs further investigation. Thus, much seems to remain to be clarified on the action of IL-6 on angiogenesis in vivo, especially in patients with Castleman's disease.

DISCLOSURE OF THE INVENTION

The present invention is intended to provide an agent that lowers blood levels of VEGF and an agent that inhibits angiogenesis.

The inventors of the present invention have found that L-6 antagonists such as anti-IL-6 receptor antibody inhibit angiogenesis in lymph nodes by lowering blood levels of VEGF in patients with Castleman's disease, especially patients with MCD, resulting in the disappearance of new blood vessels into lymph follicles, and thus L-6 antagonists such as anti-IL-6 receptor antibody are effective as blood VEGF level-lowering agents and, by lowering VEGF levels, for the prevention and/or treatment of angiogenesis, and thereby have completed the present invention.

Thus, the present invention provides (1) a blood VEGF level-lowering agent and a angiogenesis inhibitor comprising an IL-6 antagonist as an active ingredient.

The present invention also provides (2) a blood VEGF level-lowering agent and a angiogenesis inhibitor comprising an antibody against IL-6 receptor as an active ingredient.

The present invention also provides (3) a blood VEGF level-lowering agent and a angiogenesis inhibitor comprising a monoclonal antibody against IL-6 receptor as an active ingredient.

The present invention also provides (4) a blood VEGF level-lowering agent and a angiogenesis inhibitor comprising a monoclonal antibody against human IL-6 receptor as an active ingredient. The monoclonal antibody against human IL-6 receptor is preferably PM-1 antibody.

The present invention also provides (5) a blood VEGF level-lowering agent and a angiogenesis inhibitor comprising a monoclonal antibody against mouse IL-6 receptor as an active ingredient. The monoclonal antibody against mouse IL-6 receptor is preferably MR16-1 antibody.

The present invention also provides (6) a blood VEGF level-lowering agent and a angiogenesis inhibitor comprising a recombinant antibody against IL-6 receptor as an active ingredient. The recombinant antibody against IL-6 receptor preferably has the constant region (C region) of a human antibody.

The present invention also provides (7) a blood VEGF level-lowering agent and a angiogenesis inhibitor comprising a chimeric antibody or a humanized antibody against IL-6 receptor as an active ingredient.

The present invention also provides (8) a blood VEGF level-lowering agent and a angiogenesis inhibitor comprising a humanized PM-1 antibody as an active ingredient. According to the present invention, the angiogenesis inhibitor includes an angiogenesis-prevention agent, which inhibits the formation of a new blood vessel and/or an angiogenesis-treatment agent, which extinguishes a blood vessel newly formed by a disease, and preferably the angiogenesis inhibitor means is an angiogenesis prevention agent.

The present invention also provides (9) a treatment agent for Multicentric Castleman's disease (MCD), comprising, as an active ingredient, an IL-6 antagonist.

The present invention further provides (10) an alleviation agent for disease relating to the angiogenesis, comprising, as an active ingredient, an IL-6 antagonist.

The inhibition of the angiogenesis is caused by lowering the blood VEGF level.

BRIEF EXPLANATION OF THE DRAWING

FIG. 1 is a graph, which shows that a serum VEGF level in a patient having Castleman's disease is lowered during treatment of the patent with an anti-IL-6R monoclonal antibody.

BEST MODE FOR CARRYING OUT THE INVENTION

IL-6 antagonists for use in the present invention may be of any origin, any type, and any form, as long as they exhibit the effect of lowering blood VEGF levels and/or inhibiting angiogenesis.

IL-6 antagonists are substances that block signal transduction by IL-6 and inhibit the biological activity of IL-6. IL-6 antagonists are substances that preferably have an inhibitory action on the binding to any of IL-6, IL-6 receptor or gp130. As IL-6 antagonists, there can be mentioned, for example, anti-IL-6 antibody, anti-IL-6 receptor antibody, ant-gp130 antibody, reshaped IL-6, soluble reshaped IL-6 receptor, or partial peptides of IL-6 or IL-6 receptor, as well as low molecular weight substances that exhibit activities similar to them.

Anti-IL-6 antibodies for use in the present invention can be obtained as polyclonal or monoclonal antibodies using a known method. As the anti-IL-6 antibodies for use in the present invention, monoclonal antibodies of, in particular, a mammalian origin are preferred. Monoclonal antibodies of a mammalian origin include those produced by a hybridoma and those produced by a host which has been transformed by gene engineering technology with an expression vector containing the antibody gene. These antibodies, via binding to IL-6, block the binding of IL-6 to IL-6 receptor, and thereby block the propagation of biological activity of IL-6 into the cell.

Examples of such antibodies include MH166 antibody (Matsuda, et al., Eur. J. Immunology (1988) 18, 951-956), or SK2 antibody (Sato, et al., The 21st General Meeting of the Japanese Society for Immunology, Gakujutu Kiroku (1991) 21, 166) etc.

A hybridoma that produces anti-IL-6 antibody can be basically constructed using a known procedure as described bellow. Thus, IL-6 is used as a sensitizing antigen, which is immunized in the conventional method of immunization, and the immune cells thus obtained are fused with known parent cells in a conventional cell fusion process, followed by a conventional screening method to screen monoclonal antibody-producing cells.

Specifically, anti-IL-6 antibodies may be obtained in the following manner. For example, human IL-6 used as the sensitizing antigen for obtaining antibody can be obtained using the IL-6 gene/amino acid sequence disclosed in Eur. J. Biochem. (1987) 168, 543-550; J. Immunol. (1988) 140, 1534-1541, or Agr. Biol. Chem. (1990) 54, 2685-2688.

After the gene sequence of IL-6 was inserted into a known expression vector to transform a suitable host cell, the IL-6 protein of interest may be purified from the host cell or a culture supernatant thereof by a known method, and the purified IL-6 protein may be used as the sensitizing antigen. Alternatively, a fusion protein of the IL-6 protein and another protein may be used as the sensitizing antigen.

Anti-IL-6 receptor antibodies for use in the present invention can be obtained as polyclonal or monoclonal antibodies using a known method. As the anti-IL-6 receptor antibodies for use in the present invention, monoclonal antibodies of, in particular, a mammalian origin are preferred. Monoclonal antibodies of a mammalian origin include those produced by a hybridoma and those produced by a host which has been transformed by gene engineering technology with an expression vector containing the antibody gene. These antibodies, via binding to IL-6, block the binding of IL-6 to IL-6 receptor, and thereby block the propagation of biological activity of IL-6 into the cell.

Examples of such antibodies include MR16-1 antibody (Tamura, T. et al., Proc. Natl. Acad. Sci. USA (1993) 90, 11924-11928), PM-1 antibody (Hirata, Y. et al., J. Immunology (1989) 143, 2900-2906), AUK12-20 antibody, AUK64-7 antibody or AUK146-15 antibody (International Patent Application WO 92-19759), and the like. Among them, PM-1 antibody is most preferred.

Incidentally, the hybridoma cell line which produces PM-1 antibody has been internationally deposited under the provisions of the Budapest Treaty as PM-1 on Jul. 12, 1988 with the National Institute of Bioscience and Human Technology, Agency of Industrial Science and Technology (1-3, Higashi 1-chome, Tsukuba city, Ibaraki Pref., Japan), as FERM BP-2998. Also, the hybridoma cell line which produces MR16-1 antibody has been internationally deposited under the provisions of the Budapest Treaty as Rat-mouse hybridoma MR16-1 on Mar. 13, 1997 with the National Institute of Bioscience and Human Technology, Agency of Industrial Science and Technology (1-3, Higashi 1-chome, Tsukuba city, Ibaraki Pref., Japan) as FERM BP-5875.

A hybridoma that produces anti-IL-6 receptor monoclonal antibody can be basically constructed using a known procedure as described bellow. Thus, IL-6 receptor is used as a sensitizing antigen, which is used to immunize in the conventional method of immunization, and the immune cells thus obtained are fused with known parent cells in a conventional cell fusion process, followed by a conventional screening method to screen monoclonal antibody-producing cells.

Specifically, anti-IL-6 receptor antibodies may be obtained in the following manner. For example, human IL-6 receptor used as the sensitizing antigen for obtaining antibody can be obtained using the IL-6 receptor gene/amino acid sequence disclosed in European Patent Application No. EP 325474, and mouse IL-6 receptor can be obtained using the IL-6 receptor gene/amino acid sequence disclosed in Japanese Unexamined Patent Publication (Kokai) No. 3-155795.

There are two types of IL-6 receptor: IL-6 receptor expressed on the cell membrane, and IL-6 receptor detached from the cell membrane (Soluble IL-6 Receptor; Yasukawa et al., J. Biochem. (1990) 108, 673-676). Soluble IL-6 receptor antibody is composed substantially of the extracellular region of IL-6 receptor bound to the cell membrane, and is different from the membrane-bound IL-6 receptor in that the former lacks the transmembrane region or both of the transmembrane region and the intracellular region. IL-6 receptor protein may be any IL-6 receptor, as long as it can be used as a sensitizing antigen for preparing anti-IL-6 receptor antibody for use in the present invention.

After a gene encoding IL-6 receptor has been inserted into a known expression vector system to transform an appropriate host cell, the desired IL-6 receptor protein may be purified from the host cell or a culture supernatant thereof using a known method, and the IL-6 receptor protein thus purified may be used as the sensitizing antigen. Alternatively, cells that express IL-6 receptor protein or a fusion protein of IL-6 receptor protein and another protein may be used as the sensitizing antigen.

*Escherichia coli* (*E. coli*) containing a plasmid pIBIBSF2R that comprises cDNA encoding human IL-6 receptor has been internationally deposited under the provisions of the Budapest Treaty as HB101-pIBIBSF2R on Jan. 9, 1989 with the National Institute of Bioscience and Human Technology, Agency of Industrial Science and Technology (1-3, Higashi 1-chome, Tsukuba city, Ibaraki Pref., Japan) as FERM BP-2232.

Anti-gp130 antibodies for use in the present invention can be obtained as polyclonal or monoclonal antibodies using a known method. As the anti-gp130 antibodies for use in the present invention, monoclonal antibodies of, in particular, a mammalian origin are preferred. Monoclonal antibodies of a mammalian origin include those produced by a hybridoma and those produced by a host which has been transformed by gene engineering technology with an expression vector containing the antibody gene. These antibodies, via binding to gp130, block the binding of gp130 to the IL-6/IL-6 receptor complex, and thereby block the propagation of biological activity of IL-6 into the cell.

Examples of such antibodies include AM64 antibody (Japanese Unexamined Patent Publication (Kokai) No. 3-219894), 4B11 antibody and 2H4antibody (U.S. Pat. No. 5,571,513), B-S12 antibody and B-P8 antibody (Japanese Unexamined Patent Publication (Kokai) No. 8-291199) etc.

A hybridoma that produces anti-gp130 antibody can be basically constructed using a known procedure as described bellow. Thus, gp130 is used as a sensitizing antigen, which is used to immunize in the conventional method of immunization, and the immune cells thus obtained are fused with known parent cells in a conventional cell fusion process, followed by a conventional screening method to screen monoclonal antibody-producing cells.

Specifically, monoclonal antibodies may be obtained in the following manner. For example, gp130 used as the sensitizing antigen for obtaining antibody can be obtained using the gp130 gene/amino acid sequence disclosed in European Patent Application No. EP 411946.

The gene sequence of gp130 may be inserted into a known expression vector, and said vector is used to transform a suitable host cell. From the host cell or a culture supernatant therefrom, the gp130 protein of interest may be purified by a known method, and the purified IL-6 protein may be used as the sensitizing antigen. Alternatively, cells expressing gp130, or a fusion protein of the gp130 protein and another protein may be used as the sensitizing antigen.

Preferably, mammals to be immunized with the sensitizing antigen are selected in consideration of their compatibility with the parent cells for use in cell fusion and they generally include, but are not limited to, rodents such as mice, rats and hamsters.

Immunization of animals with a sensitizing antigen is carried out using a known method. A general method, for example, involves intraperitoneal or subcutaneous administration of a sensitizing antigen to the mammal. Specifically, a sensitizing antigen which was diluted and suspended in an appropriate amount of phosphate buffered saline (PBS) or physiological saline etc. is mixed with an appropriate amount of a common adjuvant such as Freund's complete adjuvant. After being emulsified, it is preferably administered to a mammal, for several times, every 4 to 21 days. Additionally a suitable carrier may be used at the time of immunization of the sensitizing antigen.

After the immunization and confirmation of an increase in the desired antibody levels in the serum by a conventional method, immune cells are taken out from the mammal and are subjected to cell fusion. As preferred immune cells that are subjected to cell fusion, there can be specifically mentioned spleen cells.

Mammalian myeloma cells as the other parent cells which are subjected to cell fusion with the above-mentioned immune cells preferably include various known cell lines such as P3×63Ag8.653 (Kearney, J. F. et al., J. Immunol. (1979) 123, 1548-1550), P3×63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), FO (de St. Groth, S. F. et al., J. Immunol. Methods (1980) 35, 1-21), S194 (Trowbridge, I. S., J. Exp. Med. (1978) 148, 313-323), R210 (Galfre, G. et al., Nature (1979) 217, 131-133) and the like, which may be used as appropriate.

Cell fusion between the above immune cells and myeloma cells may be essentially conducted in accordance with a known method such as that described in Milstein et al. (Kohler, G. and Milstein, C., Methods Enzymol. (1981) 73, 3-46) and the like.

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and an adjuvant such as dimethyl sulfoxide may be added as desired to enhance the efficiency of fusion.

The preferred ratio of the immune cells and the myeloma cells for use is, for example, 1 to 10 times more immune cells than the myeloma cells. Examples of culture media to be used for the above cell fusion include, for example, RPMI 1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of 1000 to 6000, is added at a concentration of 30 to 60% (w/v) and mixed to obtain the desired fusion cells (hybridomas). Then, by repeating a sequential addition of a suitable culture liquid and centrifugation to remove the supernatant, cell fusion agents etc. that are undesirable for the growth of the hybridoma can be removed.

Said hybridoma is selected by culturing in the conventional selection medium, for example, HAT culture medium (a culture liquid containing hypoxanthine, aminopterin, and thymidine). Culturing in said HAT culture medium is continued generally for the period of time sufficient to effect killing of cells other than the desired hybridoma (non-fusion cells), generally several days to several weeks. The conventional limiting dilution method is conducted in which the hybridomas producing the desired antibody are screened and cloned.

In addition to obtaining the above hybridoma by immunizing an animal other than the human with an antigen, it is also possible to sensitize human lymphocytes in vitro with the desired antigen protein or antigen-expressing cells, and the resulting sensitized B-lymphocytes are fused with a myeloma cell for example U266, having the ability of dividing permanently to obtain a hybridoma that produces the desired human antibody having the activity of binding to the desired antigen or antigen-expressing cells (Japanese Post-examined Patent Publication (Kokoku) 1-59878). Furthermore, a transgenic animal having a repertoire of human antibody genes is immunized with the antigen or antigen-expressing cells to obtain the desired human antibody according to the above-mentioned method (see International Patent Application WO 93/12227, WO 92/03918, WO 94/02602, WO 94/25585, WO 96/34096 and WO 96/33735).

The monoclonal antibody-producing hybridomas thus constructed can be subcultured in the conventional culture liquid, or can be stored for a prolonged period of time in liquid nitrogen.

In order to obtain monoclonal antibodies from said hybridoma, there can be used a method in which said hybridoma is cultured in the conventional method and the antibodies are obtained as the supernatant, or a method in which the hybridoma is implanted to and grown in a mammal compatible with said hybridoma and the antibodies are obtained as the ascites. The former method is suitable for obtaining high-purity antibodies, whereas the latter is suitable for a large scale production of antibodies.

For example, an anti-IL-6 receptor antibody-producing hybridoma can be prepared by a method disclosed in Japanese Unexamined Patent Publication (Kokai) No. 3-139293. There may be used a method in which the PM-1 antibody-producing hybridoma that has been internationally deposited under the provisions of the Budapest Treaty on Jul. 12, 1988 with the National Institute of Bioscience and Human Technology, Agency of Industrial Science and Technology (1-3, Higashi 1-chome, Tsukuba city, Ibaraki Pref., Japan) as FERM BP-2998 is intraperitoneally injected to BALB/c mice to obtain ascites, from which ascites PM-1 antibody may be purified, or a method in which the hybridoma is cultured in a RPMI 1640 medium containing 10% bovine fetal serum, 5% BM-Codimed H1 (manufactured by Boehringer Mannheim), the hybridoma SFM medium (manufactured by GIBCO BRL), the PFHM-II medium (manufactured by GIBCO BRL) or the like, from the culture supernatant of which PM-1 antibody may be purified.

In accordance with the present invention, as a monoclonal antibody, there can be used a recombinant antibody that was produced by cloning an antibody gene from a hybridoma and the gene is then integrated into an appropriate vector, which is introduced into a host to produce the recombinant antibody using gene recombinant technology (see, for example, Borrebaeck, C. A. K. and Larrick, J. W., THERAPEUTIC MONOCLONAL ANTIBODIES, published in the United Kingdom by MACMILLAN PUBLISHERS LTD. 1990).

Specifically, mRNA encoding the variable region (V region) of the antibody is isolated from the cell that produces the antibody of interest, for example a hybridoma. The isolation of mRNA is conducted by preparing total RNA by a known method such as the guanidine ultracentrifuge method (Chirgwin, J. M. et al., Biochemistry (1979) 18, 5294-5299), the AGPC method (Chomczynski, P. et al., Anal. Biochem. (1987) 162, 156-159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. U.S.A. (1988) 85, 8998-9002; Belyavsky, A. et al., Nucleic Acids Res. (1989) 17, 2919-2932), which employs PCR, may be used. The desired DNA fragment is purified from the PCR product obtained and may be ligated to vector DNA. Moreover, a recombinant vector is constructed therefrom and then is introduced into *E. coli* etc., from which colonies are selected to prepare the desired recombinant vector. The base sequence of the desired DNA may be confirmed by a known method such as the dideoxy method.

Once DNA encoding the V region of the desired antibody has been obtained, it may be ligated to DNA encoding the constant region (C region) of the desired antibody, which is then integrated into an expression vector. Alternatively, DNA encoding the V region of the antibody may be integrated into an expression vector which already contains DNA encoding the C region of the antibody.

In order to produce antibody for use in the present invention, the antibody gene is integrated into an expression vector so as to be expressed under the control of the expression regulatory region, for example an enhancer and/or a promoter. Subsequently, the expression vector is transformed into a host cell and the antibody can then be expressed therein.

In accordance with the present invention, artificially altered recombinant antibodies such as chimeric antibody and humanized antibody can be used for the purpose of lowering heterologous antigenicity against humans. These altered antibody can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Application WO 92-19759). Using this known method, chimeric antibody useful for the present invention can be obtained.

Plasmids containing the L chain V region or the H chain V region of chimeric PM-1 antibody have each been designated as pPM-k3 and pPM-h1, respectively, and *E. coli* having a respective plasmid has been internationally deposited under the provisions of the Budapest Treaty as NCIMB40366 and NCIMB40362 on Feb. 11, 1991 with the National Collections of Industrial and Marine Bacteria Limited.

Humanized antibody which is also called reshaped human antibody has been made by implanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Application WO 92-19759).

Specifically, a DNA sequence which was designed to ligate the CDR of mouse antibody with the framework region (FR) of human antibody is synthesized from several divided oligonucleotides having sections overlapping with one another at the ends thereof. The DNA thus obtained is ligated to DNA encoding the C region of human antibody and then is incorporated into an expression vector, which is introduced into a host for antibody production (see European Patent Application EP 239400 and International Patent Application WO 92-19759).

For the FR of human antibody ligated through CDR, the CDR that has a favorable antigen-binding site is selected. When desired, amino acids in the FR of antibody V region may be substituted so that the CDR of humanized antibody may form an appropriate antigen binding site (Sato, K. et al., Cancer Res. (1993) 53, 851-856).

As the C region of human antibody, there can be used, for example, Cγ1, Cγ2, Cγ3, or Cγ4 can be used. The C region of human antibody may also be modified in order to improve the stability of the antibody and of the production thereof.

Chimeric antibody consists of the V region of antibody of a human origin other than humans and the C region of human antibody, and humanized antibody consists of the complementarity determining region of antibody of a human origin other than humans and the framework region and the C region of human antibody, with their antigenicity in the human body being decreased, and thus are useful as antibody for use in the present invention.

As a preferred embodiment of humanized antibody for use in the present invention, there can be mentioned humanized PM-1 antibody (see International Patent Application WO 92-19759).

Antibody genes constructed as mentioned above may be expressed and obtained in a known manner. In the case of mammalian cells, expression may be accomplished using a DNA in which a commonly used useful promoter, an antibody gene to be expressed, and the poly A signal have been operably linked at 3' downstream thereof, or a vector containing it. As the promoter/enhancer, for example, there can be mentioned human cytomegalovirus immediate early promoter/enhancer.

Additionally, as the promoter/enhancer which can be used for expression of antibody for use in the present invention, there can be used viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Mulligan, R. C. et al., Nature (1979) 277, 108-114) when SV40 promoter/enhancer is used, and by the method of Mizushima, S. et al. (Mizushima, S. and Nagata, S., Nucleic Acids Res. (1990) 18, 5322) when HEF1α promoter/enhancer is used.

In the case of *E. coli*, expression may be conducted by operably linking a commonly used promoter, a signal sequence for antibody secretion, and an antibody gene to be expressed, followed by expression thereof. As the promoter, for example, there can be mentioned lacz promoter and araB promoter. The method of Ward et al. (Ward, E. S. et al., Nature (1989) 341, 544-546; Ward, E. S. et al., FASEB J. (1992) 6, 2422-2427) may be used when lacz promoter is used, and the method of Better et al. (Better, M. et al., Science (1988) 240, 1041-1043) may be used when araB promoter is used.

As a signal sequence for antibody secretion, when produced in the periplasm of *E. coli*, the pelB signal sequence (Lei, S. P. et al., J. Bacteriol. (1987) 169, 4379-4383) can be used. After separating the antibody produced in the periplasm, the structure of the antibody is appropriately refolded before use (see, for example, WO 96-30394).

As the origin of replication, there can be used those derived from SV40, polyoma virus, adenovirus, bovine papilloma virus (BPV), and the like. Furthermore, for amplification of gene copy number in the host cell system, expression vectors can include, as selectable markers, the aminoglycoside transferase (APH) gene, the thymidine kinase (TK) gene, *E. coli* xanthine guaninephosphoribosyl transferase (Ecogpt) gene, the dihydrofolate reductase (dhfr) gene, and the like.

For the production of antibody for use in the present invention, any production system can be used, and the production system of antibody preparation comprises the in vitro or the in vivo production system. As the in vitro production system, there can be mentioned a production system which employs eukaryotic cells and a production system which employs prokaryotic cells.

When eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus oocytes*, or (3) insect cells such as sf9, sf21, and Tn5. Known plant cells include, for example, those derived from the *Nicotiana tabacum* which is subjected to callus culture. Known fungal cells include yeasts such as genus *Saccharomyces*, more specifically *Saccharomyces cereviceae*, or filamentous fungi such as the *Aspergillus* family, more specifically *Aspergillus niger*.

When prokaryotic cells are used, there are the production systems which employ bacterial cells. Known bacterial cells include *Escherichia coli* and *Bacillus subtilis*.

By introducing, via transformation, the gene of the desired antibody into these cells and culturing the transformed cells in vitro, the antibody can be obtained. Culturing is conducted in the known methods. For example, as the culture liquid for mammalian cells, DMEM, MEM, RPMI1640, IMDM and the like can be used, and serum supplements such as fetal calf serum (FCS) may be used in combination. In addition, antibodies may be produced in vivo by implanting cells into which the antibody gene has been introduced into the abdominal cavity of an animal, and the like.

As in vivo production systems, there can be mentioned those which employ animals and those which employ plants.

When animals are used, there are the production systems which employ mammals and insects.

As mammals, goats, pigs, sheep, mice, and cattle can be used (Vicki Glaser, SPECTRUM Biotechnology Applications, 1993). Also, as insects silkworms can be used, and in the case of plants, tobacco, for example, can be used.

Antibody genes are introduced into these animals and plants, in which the genes are produced and then collected. For example, antibody genes are inserted into the middle of a gene encoding a protein, which is inherently produced in the milk such as goat β casein, to prepare fusion genes. DNA fragments containing the fusion gene into which the antibody gene has been inserted are injected to a goat embryo, and the embryo is introduced into a female goat. The desired antibody is obtained from the milk produced by a transgenic goat borne to the goat who received the embryo or the offspring thereof. In order to increase the amount of milk containing the desired antibody produced by the transgenic goat, hormones may be given to the transgenic goat as appropriate (Ebert, K. M. et al., Bio/Technology (1994) 12, 699-702).

When silkworms are used, the silkworms are infected with baculovirus into which the desired antibody gene has been inserted, and the desired antibody can be obtained from the body fluid of the silkworm (Maeda, S. et al., Nature (1985) 315, 592-594). Moreover, when tobacco is used, the desired antibody gene is inserted into an expression vector for plants, for example pMON 530, and then the vector is introduced into a bacterium such as *Agrobacterium tumefaciens*. The bacterium is then infected to tobacco such as *Nicotiana tabacum* to obtain the desired antibody from the leaves of the tobacco (Julian, K.-C. Ma et al., Eur. J. Immunol. (1994) 24, 131-138).

When antibody is produced in an in vitro or in vivo production systems, as mentioned above, DNA encoding the heavy chain (H chain) or light chain (L chain) of antibody is separately incorporated into an expression vector and the hosts are transformed simultaneously, or DNA encoding the H chain and the L chain of antibody is integrated into a single expression vector and the host is transformed therewith (see International Patent Application WO 94-11523).

Antibodies for use in the present invention may be fragments of antibody or modified versions thereof as long as they are preferably used in the present invention. For example, as fragments of antibody, there may be mentioned Fab, F(ab')2, Fv or single-chain Fv (scFv) in which Fv's of H chain and L chain were ligated via a suitable linker.

Specifically antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods Enzymol. (1989) 178, 476-496; Plucktrun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. et al., TI BTECH (1991) 9, 132-137).

scFv can be obtained by ligating the V region of H chain and the V region of L chain of antibody. In the scFv, the V region of H chain and the V region of L chain are preferably ligated via a linker, preferably a peptide linker (Huston, J. S. et al., Proc. Natl. Acad. Sci. U.S.A. (1988) 85, 5879-5883). The V region of H chain and the V region of L chain in the scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA be ligated to the H chain and the L chain, respectively.

Once DNAs encoding scFv are constructed, an expression vector containing them and a host transformed with said expression vector can be obtained by a conventional method, and scFv can be obtained using the resultant host by a conventional method.

These antibody fragments can be produced by obtaining the gene thereof in a similar manner to that mentioned above, and by allowing it to be expressed in a host. "Antibody" as used in the claim of the present application encompasses these antibody fragments.

As modified antibodies, antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

Antibodies expressed and produced as described above can be separated from inside or outside of the cell or from the host and then may be purified to homogeneity. Separation and purification of antibody for use in the present invention may be accomplished by affinity chromatography. As the column used for affinity chromatography, there can be mentioned Protein A column and Protein G column. Examples of carriers for use in Protein A column include, for example, Hyper D, POROS, Sepharose F.F. and the like. In addition, commonly used methods of separation and purification for proteins can be used, without any limitation.

Chromatography other than the above affinity chromatography, filters, gel filtration, salting out, dialysis and the like may be selected and combined as appropriate, in order to separate and purify the antibodies for use in the present invention. Chromatography includes, for example, ion exchange chromatography, hydrophobic chromatography, gel-filtration and the like. These chromatographies can be applied to high performance liquid chromatography (HPLC). Also, reverse phase HPLC (rpHPLC) may be used.

The concentration of antibody obtained as above can be determined by measurement of absorbance or by ELISA and the like. Thus, when absorbance measurement is employed, the antibody obtained is appropriately diluted with PBS(−) and then the absorbance is measured at 280 nm, followed by calculation using the absorption coefficient of 1.35 OD at 1 mg/ml. When ELISA is used, measurement is conducted as follows. Thus, 100 μl of goat anti-human IgG antibody (manufactured by TAGO) diluted to 1 μg/ml in 0.1 M bicarbonate buffer, pH 9.6, is added to a 96-well plate (manufactured by Nunc), and is incubated overnight at 4° C. to immobilize the antibody. After blocking, 100 μl each of appropriately diluted antibody for use in the present invention or samples containing the antibody, or human IgG (manufactured by CAPPEL) as the standard is added, and incubated at room temperature for 1 hour.

After washing, 100 μl of 5000-fold diluted alkaline phosphatase-labelled anti-human IgG antibody (manufactured by BIO SOURCE) is added, and incubated at room temperature for 1 hour. After washing, the substrate solution is added and incubated, followed by measurement of absorbance at 405 nm using the MICROPLATE READER Model 3550 (manufactured by Bio-Rad) to calculate the concentration of the desired antibody.

Reshaped IL-6 for use in the present invention is a substance that has an activity of binding with IL-6 receptor and that does not propagate the biological activity of IL-6. Thus, though reshaped IL-6 competes with IL-6 for binding to IL-6 receptor, it does not propagate the biological activity of IL-6 and, therefore, reshaped IL-6 blocks signal transduction by IL-6.

Reshaped IL-6 may be prepared by introducing mutation by replacing amino acid residues of the amino acid sequence of IL-6. The IL-6 from which reshaped IL-6 is derived may be of any origin, but it is preferably human IL-6 considering antigenicity etc.

Specifically, the secondary structure of the amino acid sequence of IL-6 may be estimated using a known molecular modeling program such as WHATIF (Vriend et al., J. Mol. Graphics (I1990) 8, 52-56), and its effect on the overall amino acid residues to be replaced is evaluated. After determining suitable amino acid residues, mutation may be introduced using a vector containing a base sequence encoding human IL-6 gene as a template in a commonly used PCR method so as to replace amino acids, and thereby to obtain a gene encoding reshaped IL-6. This may be integrated, as appropriate, into a suitable expression vector to obtain reshaped IL-6 according to the above-mentioned methods for expression, production, and purification of recombinant antibody.

Specific examples of reshaped IL-6 has been disclosed in Brakenhoff et al., J. Biol. Chem. (1994) 269, 86-93, Saviono et al., EMBO J. (1994) 13, 1357-1367, WO 96-18648 and WO 96-17869.

Partial peptides of IL-6 or partial peptides of IL-6 receptor for use in the present invention are substances that have an activity of binding to IL-6 receptor or IL-6, respectively, and that do not propagate the biological activity of IL-6. Thus, partial peptides of IL-6 or partial peptides of IL-6 receptor bind to and capture IL-6 receptor or IL-6, respectively, so as to inhibit specifically the binding of IL-6 to IL-6 receptor. As a result, they do not propagate the biological activity of IL-6, and thereby block signal transduction by IL-6.

Partial peptides of IL-6 or partial peptides of IL-6 receptor are peptides are peptides comprising part or all of the amino acid sequence involved in the binding of IL-6 and IL-6 receptor in the amino acid sequences of IL-6 or IL-6 receptor. Such peptides comprise usually 10-80 amino acid residues, preferably 20-50 amino acid residues, and more preferably 20-40 amino acid residues.

Partial peptides of IL-6 or partial peptides of IL-6 receptor specify the regions involved in the binding of IL-6 and IL-6 receptor in the amino acid sequence of IL-6 or IL-6 receptor, and part or all of the amino acid sequence can be prepared by a commonly known method such as gene engineering technology or peptide synthesis.

In order to prepare partial peptides of IL-6 or partial peptides of IL-6 receptor by gene engineering technology, a DNA sequence encoding the desired peptide can be integrated into an expression vector so that they may be obtained according to the above-mentioned methods for expression, production, and purification of recombinant antibody.

In order to prepare partial peptides of IL-6 or partial peptides of IL-6 receptor by peptide synthesis, a commonly used method in peptide synthesis such as solid-phase synthesis or liquid-phase synthesis can be used.

Specifically, methods described in "Zoku Iyakuhinno Kaihatsu, Vol. 14: Peptide Synthesis" edited by Haruaki Yajima, Hirokawa Shoten, 1991, can be used. As the solid-phase synthesis, there can be used a method in which an amino acid corresponding to the C-terminal of the peptide to be synthesized is bound to a support insoluble in organic solvents, and then a reaction in which an amino acid of which α-amino group and a side chain functional group has been protected with a suitable protecting group is condensed one by one in the direction of the C-terminal to the N-terminal, and a reaction in which said protecting group of the α-amino group of the amino acid or the peptide bound to the resin is eliminated therefrom, are alternately repeated to extend the peptide chain. The solid-phase peptide synthesis is roughly divided in the Boc method and the Fmoc method depending on the type of protecting groups used.

After thus synthesizing the peptide of interest, a deprotecting reaction or a cleavage reaction of the peptide chain from the support may be performed. For the cleavage reaction of peptide chains, the Boc method employs hydrogen fluoride or trifluoromethanesulfonic acid, or the Fmoc method usually employs TFA. In the Boc method, the above protected peptide resin is treated in the presence of anisole in hydrogen fluoride. Subsequently, the elimination of the protecting group and the cleavage from the support may be performed to collect the peptide. Lyophilization yields crude peptide. On the other hand, in the Fmoc method, the deprotection reaction and the cleavage reaction of the peptide chain from the support may be performed in a manner similar to the one mentioned above.

The crude peptide obtained may be subjected to HPLC to separate and purify it. In its elution, a water-acetonitrile solvent commonly used in protein purification may be used under an optimal condition. Fractions corresponding to the peaks of the chromatographic profile are harvested and then lyophilized. For the peptide fractions thus purified, molecular weight analysis by mass spectroscopy, analysis of amino acid composition, or analysis of amino acid sequence is performed for identification.

Specific examples of IL-6 partial peptides and IL-6 receptor partial peptides have been disclosed in Japanese Unexamined Patent Publication (Kokai) No. 2-188600, Japanese Unexamined Patent Publication (Kokai) No. 7-324097, Japanese Unexamined Patent Publication (Kokai) No. 8-311098, and U.S. Pat. Publication U.S. Pat. No. 5,210,075.

The inhibitory activity of IL-6 signal transduction by IL-6 antagonist of the present invention can be evaluated using a commonly known method. Specifically, an IL-6-dependent human myeloma cell line (S6B45, KPMM2), human Lennert's T lymphoma cell line KT3, or IL-6-dependent HN60.BSF2 cells are cultured, IL-6 is added, and at the same time, in the presence of IL-6 antagonist, the incorporation of $^3$H labelled thymidine by the IL-6 dependent cells is determined. Alternatively, IL-6 receptor-expressing U266 cells are cultured, $^{125}$I-labelled IL-6 is added simultaneously with IL-6 antagonist, and then $^{125}$I-labelled IL-6 that bound to the IL-6 receptor-expressing cells is determined. In the above assay system, in addition to the group in which the IL-6 antagonist is present, a negative control group which contains no IL-6 antagonist is set up, and the results obtained in both of them are compared to evaluate the IL-6-inhibiting activity by IL-6 antagonist.

As is shown in the Examples below, the fact that the administration of anti-IL-6 receptor antibody caused the reduction of blood VEGF levels in patients with Castleman's disease suggested that IL-6 antagonists such as anti-IL-6 receptor antibody have an activity of lowering blood VEGF levels and inhibiting the angiogenesis.

Subjects to be treated in the present invention are mammals. Subject mammals to be treated are preferably humans.

The blood VEGF level-lowering agent and the angiogenesis inhibitor of the present invention may be administered orally or parenterally and systemically or locally. For example, intravenous injection such as drip infusion, intramuscular injection, intraperitoneal injection, subcutaneous injection, suppositories, enema, oral enteric coated tablets, and the like may be selected, and the dosage regimen may be selected as appropriate depending on the age and disease conditions of patients. The effective dose is chosen from the range of 0.01 mg to 100 mg per kg of body weight per administration. Alternatively, the dosage of 1 to 1000 mg, preferably 5 to 50 mg per patient may be selected. Preferred dosages and dosage regimens are such that in the case of an anti-IL-6 receptor antibody, effective doses are those in which free antibody is present in the blood, and specific examples are 0.5 to 40 mg/kg body weight per month (four weeks), and preferably the dosage of 1 mg to 20 mg is administered in divided amounts of once to a few times by intravenous injection such as drip infusion, subcutaneous injection etc., for example in an administration schedule of twice per week, once per week, once per two weeks, once per four weeks, and the like.

The blood VEGF level-lowering agent and the angiogenesis inhibitor of the present invention may contain pharmaceutically acceptable carriers and additives depending on the route of administration. Examples of such carriers or additives include water, a pharmaceutically acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol Vaseline, paraffin, stearyl alcohol, stearic acid, human serum albumin (HSA), mannitol, sorbitol, lactose, pharmaceutically acceptable surfactants and the like. Actual additives used are chosen from, but not limited to, the above, or combinations thereof, depending on the dosage form.

EXAMPLES

The present invention will now be explained in more detail by reference to the following working examples, reference examples, and experimental examples. It is to be noted, however, that the present invention is not limited by the examples in any way.

Example

Seven patients with Multicentric Castleman's Disease (CD) were treated with a humanized anti-IL-6 receptor antibody (humanized PM-1 antibody; described in WO 92/19759, consisting of light chain version "a" and H chain version "f"), and changes in serum levels of VEGF associated with the treatment were investigated using an ELISA method (using the ELISA kit manufactured by R&D). The antibody was dissolved in 100 ml of physiological saline, and used in drip infusion at a rate of 50 mg/body twice per week or 100 mg/body once a week by increasing the amount from 1 mg to 10 mg to 50 mg while confirming the safety of the dose. Sera before and two months after the start of the treatment and one month after the suspension of the treatment were stored at −20° C. and were used for measurement.

The result is shown in FIG. 1. The result indicated that serum levels of VEGF was clearly lowered by the administration of the humanized anti-IL-6 receptor antibody, and at the suspension of treatment they start to rise again. It was also confirmed that newly formed blood vessels in lymph nodes vessels disappeared leaving sporadic eosinophilic deposits. This fact indicates that humanized anti-IL-6 receptor antibody is effective as a blood VEGF level-lowering agent in patients with Castleman's disease, especially patients with Multicentric Castleman's Disease.

The foregoing has shown that anti-IL-6 receptor antibody reduces blood levels of VEGF, and has shown a possibility that it could be an angiogenesis-inhibiting agent, especially a preventive agent for de novo synthesis of blood vessels.

Reference Example 1

Preparation of Human Soluble IL-6 Receptor

Using a plasmid pBSF2R.236 containing cDNA that encodes IL-6 receptor obtained by the method of Yamasaki et al. (Yamasaki et al., Science (1988) 241, 825-828), soluble IL-6 receptor was prepared by the PCR method. The plasmid pBSF2R.236 was digested with a restriction enzyme Sph I to obtain IL-6 receptor cDNA, which was inserted into mp18 (manufactured by Amersham). Using a synthetic primer designed to introduce a stop codon into IL-6 receptor cDNA, mutation was introduced into IL-6 receptor cDNA by the PCR method in an in vitro mutagenesis system (manufactured by Amersham). By this procedure, the stop codon was introduced at the position of amino acid 345, and cDNA encoding soluble IL-6 receptor was obtained.

In order to express soluble IL-6 receptor in CHO cells, it was ligated to a plasmid pSV (manufactured by Pharmacia) to obtain a plasmid. pSVL344. Soluble IL-6 receptor cDNA digested with HindIII-SalI was inserted into a plasmid pECEdhfr containing the cDNA of dhfr to obtain a CHO cell-expressing plasmid pECEdhfr344.

Ten μg of plasmid pECEdhfr344 was transfected to a dhfr-CHO cell line DXB-11 (Urlaub, G. et al., Proc. Natl. Acad. Sci. USA (1980) 77, 4216-4220) by the calcium phosphate precipitation method (Chen, C. et al., Mol. Cell. Biol. (1987) 7, 2745-2751). The transfected CHO cells were cultured for three weeks in a nucleoside-free αMEM selection medium containing 1 mM glutamine, 10% dialyzed FCS, 100 U/ml penicillin and 100 μ/ml streptomycin.

The selected CHO cells were screened by the limiting dilution method to obtain a single CHO cell clone. The CHO cell clone was amplified with 20 nM-200 nM of methotrexate to investigate a human soluble IL-6 receptor-producing CHO cell line 5E27. The CHO cell line 5E27 was cultured in a Iscov's modified Dulbecco's Medium (IMDM, manufactured by Gibco) supplemented with 5% FBS. The culture supernatant was collected and the concentration of soluble IL-6 receptor in the culture supernatant was determined by ELISA. The result confirmed the presence of soluble IL-6 receptor in the culture supernatant.

Reference Example 2

Preparation of Anti-Human IL-6 Antibody

Ten μg of tissue-type IL-6 (Hirano et al., Immunol. Lett. (1988) 17, 41) was used with Freund's complete adjuvant to immunize BALB/c mice, and this was repeated every week until anti-IL-6 antibody can be detected in the serum. Immune cells were removed from the local lymph nodes, and were fused with a myeloma cell line P3U1 using polyethylene glycol 1500. Hybridomas were selected by the method of Oi et al. (Selective Methods in Cellular Immunology, W.H. Freeman and Co., San Francisco, 351, 19080) using the HAT culture medium to establish a hybridoma producing anti-human IL-6 antibody.

The hybridoma producing anti-human IL-6 antibody was subjected to an IL-6 binding assay in the following manner. Thus, a 96-well microtiter plate (manufactured by Dynatech Laboratories, Inc., Alexandria, Va.) made of flexible polyvinyl was coated overnight with 100 µl of goat anti-mouse Ig (10 µl/ml, manufactured by Cooper Biomedical, Inc., Malvern, Pa.) in 0.1 M carbonate hydrogen carbonate buffer (pH 9.6) at 4° C. Then, the plate was treated in 100 µl of PBS containing 1% bovine serum albumin (BSA) at room temperature for 2 hours.

After this was washed in PBS, 100 µl of the hybridoma culture supernatant was added to each well, and incubated overnight at 4° C. After washing the plate, $^{125}$I-labelled recombinant type IL-6 was added to each well to 2000 cpm/0.5 ng/well, and after washing, radioactivity of each well was measured by a gamma counter (Beckman Gamma 9000, Beckman Instruments, Fullerton, Calif.). Of 216 hybridoma clones, 32 hybridoma clones were positive in the IL-6 binding assay. From among these clones, finally, MH166.BSF2, that was stable, was selected. Anti-IL-6 antibody MH166 has a subtype of IgG1 K type.

Then, using a IL-6-dependent mouse hybridoma clone MH60.BSF2, a neutralizing activity with regard to the growth of the hybridoma by MH166 antibody was investigated. MH60.BSF2 cells were aliquoted to $1\times10^4/200$ µl/well, to which a sample containing MH166 antibody was added, and cultured for 48 hours. After adding 0.5 µCi/well of $^3$H-thymidine (New England Nuclear, Boston, Mass.), culturing was continued for further six hours. The cells were placed on a glass filter paper, and were treated by an automated harvester (Labo Mash Science Co., Tokyo, Japan). As the control, rabbit anti-IL-6 antibody was used.

As a result, MH166 antibody inhibited $^3$H-thymidine incorporation by MH60.BSF2 cells induced by IL-6 in a dose dependent manner. This revealed that MH166 antibody neutralizes the activity of IL-6.

Reference Example 3

Preparation of Anti-Human IL-6 Receptor Antibody

Anti-IL-6 receptor antibody MT18 prepared by the method of Hirata et al. (Hirata, Y. et al., J. Immunol. (1989) 143, 2900-2906) was conjugated to a CNBr-activated Sepharose 4B (manufactured by Pharmacia Fine Chemicals, Piscataway, N.J.) to purify IL-6 receptor (Yamasaki et al., Science (1988) 241, 825-828). A human myeloma cell line U266 was solubilized with 1 mM p-paraaminophenylmethanesulfonyl fluoride hydrochloride (manufactured by (manufactured by Wako Pure Chemicals) (digitonin buffer) containing 1% digitonin (manufactured by Wako Pure Chemicals), 10 mM triethanolamine (pH 7.8), and 0.15 M NaCl, and was mixed with MT18 antibody conjugated to Sepharose 4B beads. Subsequently, beds were washed six times in the digitonin buffer to prepare a partially purified IL-6 receptor.

BALB/c mice were immunized with the above partially purified IL-6 receptor obtained from $3\times10^9$ U266 cells four times every ten days, and then a hybridoma was prepared according to a standard method. The culture supernatant of the hybridoma from growth-positive wells were examined for the binding activity to IL-6 receptor in the following manner. $5\times10^7$ U266 cells were labelled with $^{35}$S-methionine (2.5 mCi), and were solubilized with the above digitonin buffer.

The solubilized U266 cells were mixed with 0.04 ml of MT18 antibody conjugated to Sepharose 4B beads, and then washed for six times in the digitonin buffer. Using 0.25 ml of the digitonin buffer (pH 3.4), $^{35}$S-methionine-labelled IL-6 receptor was eluted, which was neutralized with 0.025 ml of 1M Tris, pH 7.4.

0.05 ml of the hybridoma culture supernatant was mixed with 0.01 ml Protein G Sepharose (manufactured by Pharmacia). After washing, the Sepharose was incubated with 0.005 ml solution of $^{35}$S-labelled IL-6 receptor solution. The immunoprecipitated substances were analyzed by SDS-PAGE to study the culture supernatant of hybridoma that reacts with IL-6 receptor. As a result, a reaction-positive hybridoma clone PM-1 (FERM BP-2998) was established. Antibody produced from the hybridoma PM-1 had the IgG1 κ subtype.

The activity of the antibody produced by the hybridoma PM-1 to inhibit the binding of IL-6 to IL-6 receptor was evaluated using the human myeloma cell line U266. Human recombinant IL-6 was prepared from *E. coli* (Hirano et al., Immunol. Lett. (1988) 17, 41-45), and was labelled with $^{125}$I using the Bolton-Hunter reagent (New England Nuclear, Boston, Mass.) (Taga et al., J. Exp. Med. (1987) 166, 967-981).

$4\times10^5$ U266 cells were cultured with a culture supernatant of 70% (v/v) hybridoma PM-1 and 14000 CPM of $^{125}$I-labelled IL-6 for one hour. Seventy microliters of a sample was layered onto 300 µl of FCS in a 400 µl microfuge polyethylene tube, centrifuged, and then radioactivity on the cells were measured.

The result revealed that the antibody produced by the hybridoma PM-1 inhibits the binding of IL-6 to IL-6 receptor.

Reference Example 4

Preparation of Anti-Mouse IL-6 Receptor Antibody

A monoclonal antibody against mouse IL-6 receptor was prepared by the method of Saito, T. et al., J. Immunol. (1991) 147, 168-173.

CHO cells that produce soluble mouse IL-6 receptor were cultured in an IMDM culture medium supplemented with 10% FCS. From the culture supernatant, soluble mouse IL-6 receptor was purified using an affinity column in which anti-mouse IL-6 receptor antibody RS12 (see the above Saito, T. et al.) was immobilized to the Affigel 10 gel (manufactured by Biorad).

Fifty µg of soluble mouse IL-6 receptor thus obtained was mixed with Freund's complete adjuvant, which was intraperitoneally injected to the abdomen of Wistar rats. Two weeks later, the rats received booster immunization with Freund's incomplete adjuvant. On day 45, spleen cells were removed from the rats, and $2\times10^8$ of the cells were subjected to cell fusion with $1\times10^7$ mouse myeloma cells P3U1 with 50% PEG1500 (manufactured by Boehringer Mannheim) using a standard method, and hybridoma were then screened with the HAT medium.

After adding the culture supernatant to a plate coated with rabbit anti-rat IgG antibody (manufactured by Cappel), soluble mouse IL-6 receptor was reacted thereto. Then, using an ELISA method employing rabbit anti-mouse IL-6 receptor antibody and alkaline phosphatase-labelled sheep anti-rabbit IgG, hybridomas that produce antibodies against soluble mouse IL-6 receptor were screened. The hybridoma clones for which antibody production was confirmed were subjected to subscreening twice to obtain a single hybridoma clone. This clone was designated as MR16-1.

A neutralizing activity in signal transduction of mouse IL-6 by the antibody produced by this hybridoma was examined using $^3$H-thymidine incorporation that employs MH60.BSF2 cells (Matsuda, T. et al., J. Immunol. (1988) 18, 951-956). To a 96-well plate, MH60.BSF2 cells were prepared to $1\times10^4$ cells/200 µl/well. To this plate were added 10 pg/ml of mouse IL-6 and MR16-1 antibody or RS12 antibody at 12.3-1000 ng/ml, and cultured at 37° C. in 5% $CO_2$ for 44 hours, followed by the addition of 1 µCi/well of $^3$H-thymidine. Four hours later, the incorporation of $^3$H-thymidine was measured. As a result, MR16-1 antibody inhibited the $^3$H-thymidine incorporation by MH60.BSF2 cells.

Thus, it was revealed that antibody produced by the hybridoma MR16-1 (FERM BP-5875) inhibits the binding of IL-6 to IL-6 receptor.

INDUSTRIAL APPLICABILITY

The present invention indicated that IL-6 antagonists such as anti-IL-6 receptor antibody have an effect of lowering blood levels of MMP-3. Thus, it was revealed that IL-6 antagonists are effective as a blood MMP-3 level-lowering agent, a cartilage degradation inhibitor and/or a therapeutic agent for osteoarthritis.

Reference to microorganisms deposited under Rule 13-2 and depository authority
Depository Authority
Name: National Institute of Bioscience and Human Technology, Agency of Industrial Science and Technology
Address: 1-3, Higashi 1-chome, Tsukuba city, Ibaraki Pref., Japan
Microorganism
(1) Name: PM-1
  Accession number: FERM BP-2998
  Date deposited: Jul. 12, 1989
(2) Name: Rat-mouse hybridoma MR16-1
  Accession number: FERM BP-5875
  Date deposited: Mar. 13, 1997
(3) Name: HB-101-pIBIBSF2R
  Accession number: FERM BP-2232
  Date deposited: Jan. 9, 1989
Depository organ: National Collections of Industrial, Food and Marine Bacteria Limited
Address: 23 St Macher Drive, Aberdeen AB2 IRY, United Kingdom
(4) Name: *E. coli* DH5α pPM-k3
  Accession number: MCIMB 40366
  Date deposited: Feb. 12, 1991
(5) Name: *E. coli* DH5α pPM-h1
  Accession number: MCIMB 40362
  Date deposited: Feb. 12, 1991

The invention claimed is:

1. A method for lowering blood VEGF level, comprising measuring a serum level of VEGF and administering to a patient having Multicentric Castleman's Disease (MCD) and in need of lowering blood VEGF level an antibody against IL-6 receptor in an amount effective to lower blood VEGF level.

2. The method according to claim 1, wherein the antibody against IL-6 receptor is a monoclonal antibody against IL-6 receptor.

3. The method according to claim 1, in which the antibody against IL-6 receptor is a recombinant antibody.

4. The method according to claim 1, in which the antibody against IL-6 receptor is a chimeric antibody or a humanized antibody against IL-6 receptor.

5. The method of claim 1, wherein the blood VEGF level is lowered to at least 500 pg/ml.

6. A method for lowering blood VEGF level, comprising measuring a serum level of VEGF and administering to a patient having Multicentric Castleman's Disease (MCD) and in need of lowering blood VEGF level an antibody against IL-6 receptor in an amount effective to lower blood VEGF level, in which the antibody against IL-6 receptor is a monoclonal antibody against human IL-6 receptor.

7. The method according to claim 6, in which the monoclonal antibody against human IL-6 receptor is PM-1 antibody.

8. A method for lowering blood VEGF level, comprising measuring a serum level of VEGF and administering to a patient having Multicentric Castleman's Disease (MCD) and in need of lowering blood VEGF level an antibody against IL-6 receptor in an amount effective to lower blood VEGF level, in which the antibody against IL-6 receptor is a monoclonal antibody against mouse IL-6 receptor.

9. The method according to claim 8, in which the monoclonal antibody against mouse IL-6 receptor is MR16-1 antibody.

10. A method for lowering blood VEGF level, comprising measuring a serum level of VEGF and administering to a patient having Multicentric Castleman's Disease (MCD) and in need of lowering blood VEGF level an antibody against IL-6 receptor in an amount effective to lower blood VEGF level, in which the antibody against IL-6 receptor is a humanized PM-1 antibody.

11. A method for inhibiting angiogenesis, comprising measuring a serum level of VEGF and administering to a patient having Multicentric Castleman's Disease (MCD) and in need of lowering blood VEGF level an antibody against IL-6 receptor in an amount effective to inhibit angiogenesis.

12. The method according to claim 11, in which the antibody against IL-6 receptor is a monoclonal antibody against IL-6 receptor.

13. The method according to claim 12, in which the monoclonal antibody against IL-6 receptor is a monoclonal antibody against human IL-6 receptor.

14. The method according to claim 13, in which the monoclonal antibody against human IL-6 receptor is PM-1 antibody.

15. The method according to claim 12, in which the monoclonal antibody against IL-6 receptor is a monoclonal antibody against mouse IL-6 receptor.

16. The method according to claim 15, in which the monoclonal antibody against mouse IL-6 receptor is MR16-1 antibody.

17. The method according to claim 11, in which the antibody against IL-6 receptor is a recombinant antibody.

18. The method according to claim 11, in which the antibody against IL-6 receptor is a chimeric antibody or a humanized antibody against IL-6 receptor.

19. The method according to claim 18, in which the humanized antibody against IL-6 receptor is a humanized PM-1 antibody.

* * * * *